United States Patent [19]
Seng

[11] Patent Number: 6,084,663
[45] Date of Patent: Jul. 4, 2000

[54] METHOD AND AN APPARATUS FOR INSPECTION OF A PRINTED CIRCUIT BOARD ASSEMBLY

[75] Inventor: Toh Peng Seng, Singapore, Singapore

[73] Assignee: Hewlett-Packard Company, Palo Alto, Calif.

[21] Appl. No.: 08/834,945

[22] Filed: Apr. 7, 1997

[51] Int. Cl.[7] .............................. G01N 21/00; H04N 7/18
[52] U.S. Cl. ........................ 356/237.4; 348/126
[58] Field of Search .................................. 356/237, 376; 348/87, 126, 131

[56] References Cited

U.S. PATENT DOCUMENTS

| | | | |
|---|---|---|---|
| 4,926,452 | 5/1990 | Baker et al. | 372/22 |
| 4,988,202 | 1/1991 | Nayar et al. | 356/394 |
| 5,012,502 | 4/1991 | Battin et al. | 378/58 |
| 5,039,868 | 8/1991 | Kobayashi et al. | 250/572 |
| 5,064,291 | 11/1991 | Reiser | 356/372 |
| 5,097,492 | 3/1992 | Baker et al. | 372/22 |
| 5,105,149 | 4/1992 | Tokura | 348/126 |
| 5,185,638 | 2/1993 | Conzola et al. | 356/237 |
| 5,245,421 | 9/1993 | Robertson et al. | 358/101 |
| 5,260,779 | 11/1993 | Wasserman | 358/93 |
| 5,406,372 | 4/1995 | Vodanovic et al. | 348/87 |
| 5,414,513 | 5/1995 | Leib | 356/359 |
| 5,517,235 | 5/1996 | Wasserman | 348/87 |
| 5,550,583 | 8/1996 | Amir et al. | 348/87 |

FOREIGN PATENT DOCUMENTS 5-93699  4/1993  Japan ............................ 356/237

*Primary Examiner*—Frank G. Font
*Assistant Examiner*—Zandra V. Smith

[57] ABSTRACT

A method and apparatus for inspecting a printed circuit board assembly especially with surface mount devices are provided. The method and apparatus include a multiple camera set-up utilizing both color and monochrome images. A very strong white light is employed as the light source. The multiple camera setup includes frontal and oblique looking cameras to examine the printed circuited board assembly from different angles. The strong white light source provides sufficient illumination evan at a small camera aperture hence increasing the depth of field. The method and apparatus are resistant against warpage of the PCB and variations in components' height.

9 Claims, 6 Drawing Sheets

METHOD AND AN APPARATUS FOR INSPECTION OF A PRINTED CIRCUIT BOARD ASSEMBLY

BACKGROUND OF THE INVENTION

The present invention generally relates to a method and an apparatus for the inspection of a printed circuit board (PCB) assembly by machine vision means.

Automated inspection of surface mount devices (SMDs) on printed circuit boards is becoming more important as electronics devices get smaller and packing density gets higher. Automated inspection has better performance than manual inspection in terms of consistency, speed and lower cost in the long run.

The commonly found defects on a surface mount PCB assembly include missing components, misalignment, tilted components, tombstoning/open circuit, wrong components, wrong value, bridging/short circuit, bent leads, wrong polarity, extra components, lifted leads, insufficient solder, and/or excessive solder among other things.

An industrial useful inspection machine must be capable of detecting these defects reliably and fast enough to cope with the production rate. Broadly speaking, the inspection techniques can be divided into three different classes. These are the X-ray technique, laser scanning technique and machine vision technique. The X-ray technique consists of a fine focus X-ray source and appropriate detector to acquire and analyze X-ray images of the PCB assembly. Solder related defects, such as insufficient solder, excessive solder, and poor wetting, can be easily detected by the X-ray technique. However, wrong value, wrong components, wrong polarity, and bent leads cannot be inspected at all. U.S. Pat. Nos. 4,926,452, 5,097,492 and other related patents assigned to Four Pi Systems Corporation disclose inspection systems utilizing the X-ray laminography techniques. U.S. Pat. No. 5,012,502 assigned to IRT Corporation also uses the X-ray method to inspect the degree of interconnection of solder joints.

The laser scanning technique makes use of a laser triangulation method to determine the three dimensional (3D) profile of the PCB assembly. A laser beam is scanned across the surface of the PCB assembly, and the retuned beam information is used to calculate the 3D profile of the scanned path. The 3D profile of the PCB assembly is compared with that of a known good board. Wrong value and polarity cannot be inspected using this method. A small deviation from this method is the utilization of interference fringes created by the interference of two coherent laser beams on the surface of the PCB assembly. U.S. Pat. No. 5,414,513 assigned to Northdrop Grumman Corporation discloses such a method.

The machine vision technique makes use of images captured by cameras or another video source for the analysis of the PCB assembly. This technique, therefore, relies heavily on the lighting and viewing setup. U.S. Pat. Nos. 5,245,421 and 5,260,779 assigned to Control Automation of USA disclose a hemispherical lighting fixture containing hundreds of individually programmable LEDs which can be configured to achieve many combinations of lighting modes. Different solder or assembly defects are highlighted by different combinations of lighting modes. However, this method has certain limitations. For example, the light intensity generated by LEDs is usually not sufficiently bright, and thus the camera aperture needs to be wide open. A large camera aperture will limit the depth of the field of the imaging system. The detection algorithms are closely related to the lighting mode and hence the selection and programming of the hundreds of LEDs is difficult. Hence, the teaching time required for a new PCB assembly is long and complicated.

U.S. Pat. No. 5,185,638 assigned to International Business Machines Corporation discloses a computer controlled, multiple angle illumination system for inspecting defects on a PCB. The illumination system is computer controlled as to a level of intensity and adjustable as to an angle of incidence. The illumination system includes illumination control electronics, a quad quartz halogen lamp array light source, a fiber optic line converter and an illumination collection system. The viewing arrangement is not described. The desired inspection system should be reliable, accurate, immune to ambient conditions changes, and easy to set up for a new PCB assembly. The inspection system should be able to operate by ordinary technicians or operators with a minimum of programming or machine vision knowledge.

The present invention discloses a method and an apparatus that accomplishes most of these desired features, in particular, the importance of lighting and a viewing technique overcoming the deficiencies of known methods and apparatus.

SUMMARY OF THE INVENTION

The present invention uses a unique camera and lighting configuration to achieve a reliable inspection of the PCB assembly. A multiple video camera system employing both monochrome and color cameras (video source) are used. Hereinafter, in the specification and claims, the term camera will be used when referring to a video camera.

According to an embodiment of the present invention, an apparatus is provided for inspecting a printed circuit board assembly. The apparatus has a plurality of cameras and a lighting assembly. The plurality of cameras have a center camera having an optical axis arranged substantially perpendicularly to the printed circuit board assembly and four surround cameras. The four surround cameras are arranged so that their respective optical axes are arranged obliquely with respect to the printed circuit board assembly and so that the optical axes of the four surround cameras are positioned symmetrically to the optical axis of the center camera.

Preferably, the center camera is a color camera, and the surround cameras are monochrome cameras.

The four surround cameras are tilted at an angle with respect to the PCB assembly. The four monochrome cameras, therefore, acquire images of the PCB at an oblique angle. The plurality of images collectively provide an all rounded view of the PCB assembly allowing reliable and accurate analysis of the PCB assembly.

According to a second aspect of the present invention, a method is provided for inspecting a printed circuit board assembly. The method comprises the steps of: illuminating the printed circuit board assembly using a lighting assembly; viewing the printed circuit board assembly using a plurality of cameras, the plurality of cameras having a center camera having an optical axis arranged substantially perpendicularly to the printed circuit board assembly and four surround cameras, the four surround cameras arranged so that their respective optical axes are arranged obliquely with respect to the printed circuit board assembly and so that the optical axes of the four surround cameras are positioned symmetrically relative to the optical axis of the center camera; forwarding a video signal from at least one of the plurality of cameras to at least one frame grabber; and subjecting the signal to a processing step whereby defects in the printed circuit board assembly can be detected.

According to an embodiment of the present invention, the images captured by the center color camera are subjected to color imaging processing to facilitate the extraction of the components from the background. For example, the PCB itself is mostly green in color while the components are usually not. In this way, acquiring color images of the PCB assembly allows the ease of separating the components from its background.

According to another embodiment of the present invention, the four oblique monochrome cameras are positioned around the center color camera to view the PCB assembly from four different directions. These directions are denoted by North, South, East and West. The field of view of the four oblique cameras are related to the center color camera such that a common area of the PCB assembly, hereinafter denoted as a segment, can be inspected at any one time. The fields of view of any two opposite facing cameras do not overlap so that the image resolution and the total inspection area can be increased. Monochrome images can effectively capture the contrast between the solder or the leads and the PCB, but not a component and the PCB. By mounting the four monochrome cameras obliquely with respect to the PCB assembly allows height information to be computed. The oblique monochrome cameras are hence effective when used to inspect lead geometry related defects, such as lifted leads and bent leads.

According to another embodiment of the present invention, strong intensity lighting is used such that the ambient lighting condition will not affect the actual inspection condition. Quantitatively, the light source intensity should be at least ten times stronger than the ambient lighting level. Strong lighting allows the aperture, also known as an iris, of the camera lens to be adjusted small and hence increasing the depth of field of the cameras. The size of the aperture is inversely related to the depth of field of an imaging system. A large depth of field renders the imaging systems less susceptible to the change in the height or depth of the object under inspection. The change in depth and height of the PCB assembly may arise from the change in components' dimensions, the PCB thickness, and/or the warpage of the PCB. These are undesirable changes and will affect the clarity of the images acquired by the cameras. Having a large depth of field enables well-focused images to be captured regardless of these variations. A ring-shaped, white light source is preferably used. The white light source will allow different color spectrums to be equally illuminated, hence facilitating color image processing and analysis. The use of the white light source with associated color image processing is especially useful to detect color components, such as surface mounted resistors and capacitors. Some of these components may be brown, yellow, blue or orange in color. If only monochrome images are used, then it will not be possible to distinguish the colored components from the background. In monochrome images, the color of the PCB and the color components may appear to have almost the same shade of grey, hence projecting no contrast to facilitate detection.

Furthermore, the monochrome cameras mounted at an oblique angle to the PCB assembly need a large depth of field to view the entire field of view clearly. The near field and far field of an oblique viewing camera will have different depths.

According to another embodiment of the present invention, the PCB assembly is placed onto an X-Y table capable of moving the PCB assembly in the X and Y directions. A PCB assembly is usually larger than the field of view of the cameras hence the X-Y table is used to position the PCB assembly segment by segment under the camera and the lighting assembly for inspection. In this way, the entire PCB assembly will be fully inspected. The size of the segment on the PCB assembly is determined by the field of view of the cameras. In particular, for defects that are to be detected by the center color camera, the segment size is determined by the field of view of the center color camera. For IC and other components that require lead inspection for lifted, bridging, bent leads, and solder defects on leads, the segment size will be determined by the field of view of the center color camera. For IC and other components that require lead inspection for lifted, bridging, bent leads and solder defects on leads, the segment size will be determined by the field of view of the four oblique monochrome cameras.

According to another embodiment of the present invention, a rule based approach for detecting defects on the PCB assembly is used. Signatures are extracted from the plurality of images acquired by the color and monochrome cameras. The signatures are verified with a set of rules to determining the condition of the PCB assembly.

These and other advantages of the present invention are described in, and will be apparent from, the detailed description of the presently preferred embodiments and from the drawings.

DETAILED DESCRIPTION OF THE PRESENTLY PREFERRED EMBODIMENTS

Figure 1:
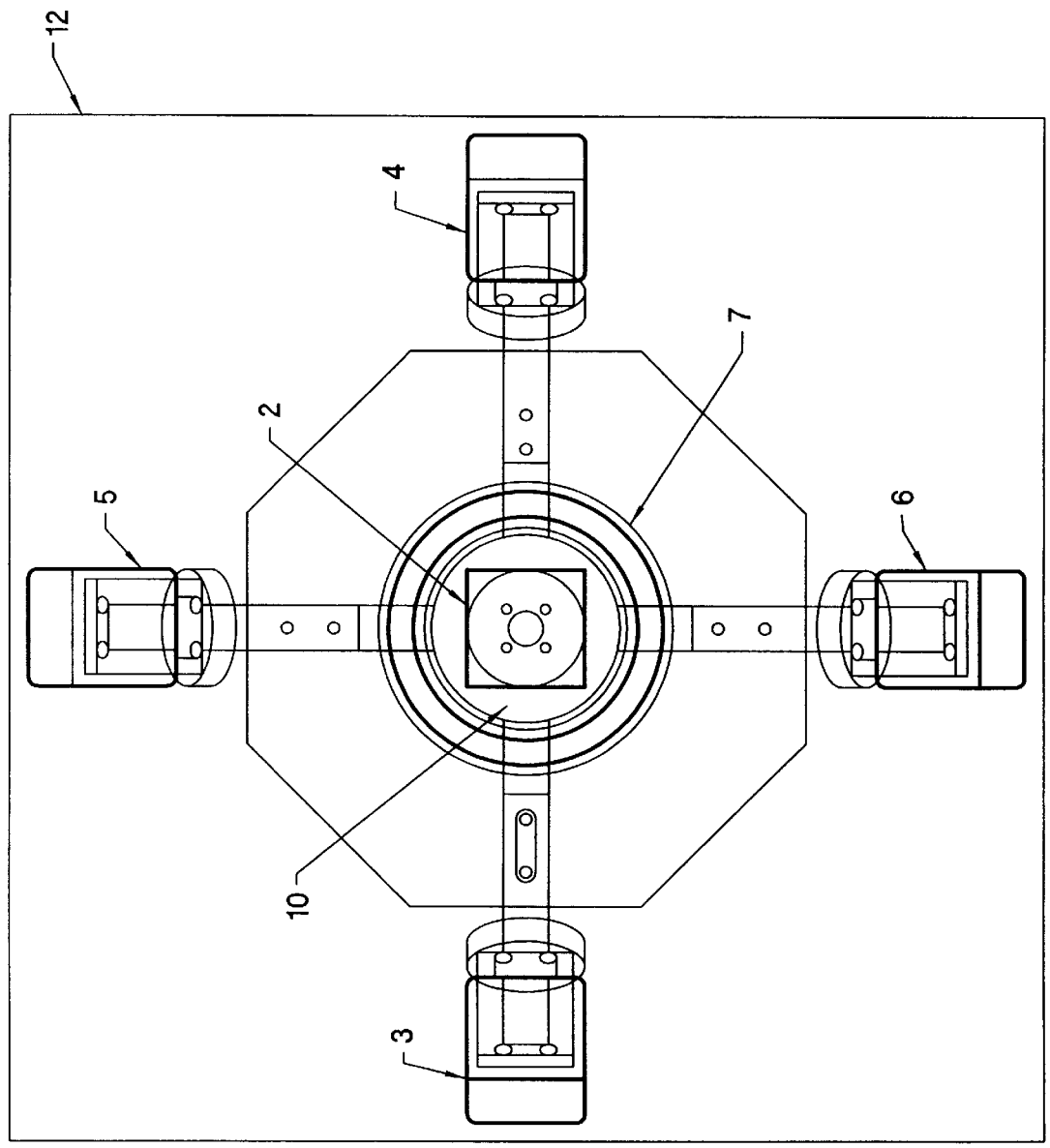
FIG. 1 illustrates a plan view of a lighting and camera assembly according to an embodiment of the invention.
Figure 2:
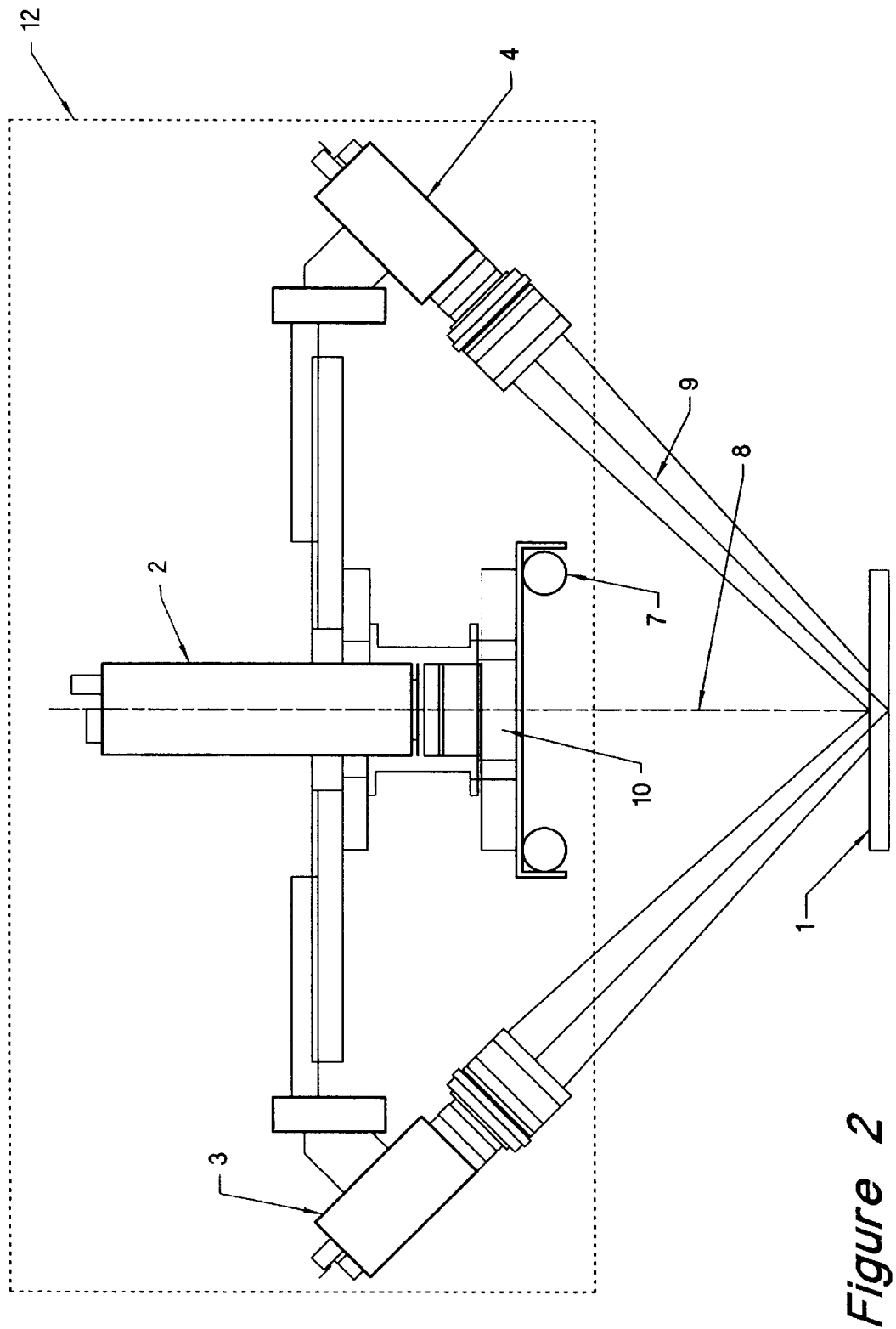
FIG. 2 illustrates a front view of the lighting and camera assembly according to an embodiment of the invention.

The present embodiment uses five cameras 2, 3, 4, 5 and 6. The center camera is a color camera 2 which views a PCB assembly 1 from the front. In other words, an optical axis 8 of the center color camera 2 is perpendicular to the PCB assembly 1. A bright ring-shaped, white light source 7 is mounted below the center color camera 2. The ring-shaped, white light source 7 has an opening 10 in its center such that the center color camera 2 views the PCB assembly 1 through the opening 10. Four monochrome cameras 3, 4, 5 and 6 are positioned symmetrically around the center color camera 2. The optical axes of the monochrome cameras 3, 4, 5 and 6 are tilted at a certain angle with respect to the surface normal from the PCB assembly 1. The center color camera 2, four oblique monochrome cameras 3, 4, 5 and 6 and the ring-shaped, white light source 7 are mounted on a common structure which is collectively called a camera and lighting assembly 12.

The four monochrome cameras are labeled as North 5, South 6, East 4 and West 3, respectively. The fields of view of any two opposite facing monochrome cameras do not overlap. For example, the North 5 and the South 6 cameras have no overlapping area. Their fields of view are denoted by 21 and 22, respectively. Similarly, this applies to the East 3 and the West 4 cameras. Their fields of view are denoted by 23 and 24, respectively. The separation between two opposite facing fields of view depends on the size of the IC used on the PCB assembly 1. The magnification factor of each of the four oblique monochrome cameras 3,4,5 and 6 are the same, thus enabling the same image processing algorithms to be applied to all of the four images.

The center color camera 2 is mainly responsible for the inspection of missing components, misalignment, tombstoning, bridging, wrong value, wrong components, wrong orientation/polarity, and solder related defects, such as insufficient solder. The frontally looking center color camera 2 does not induce any geometrical distortion in the imaging process. It is also not susceptible to obstruction by tall components.

Figure 7:
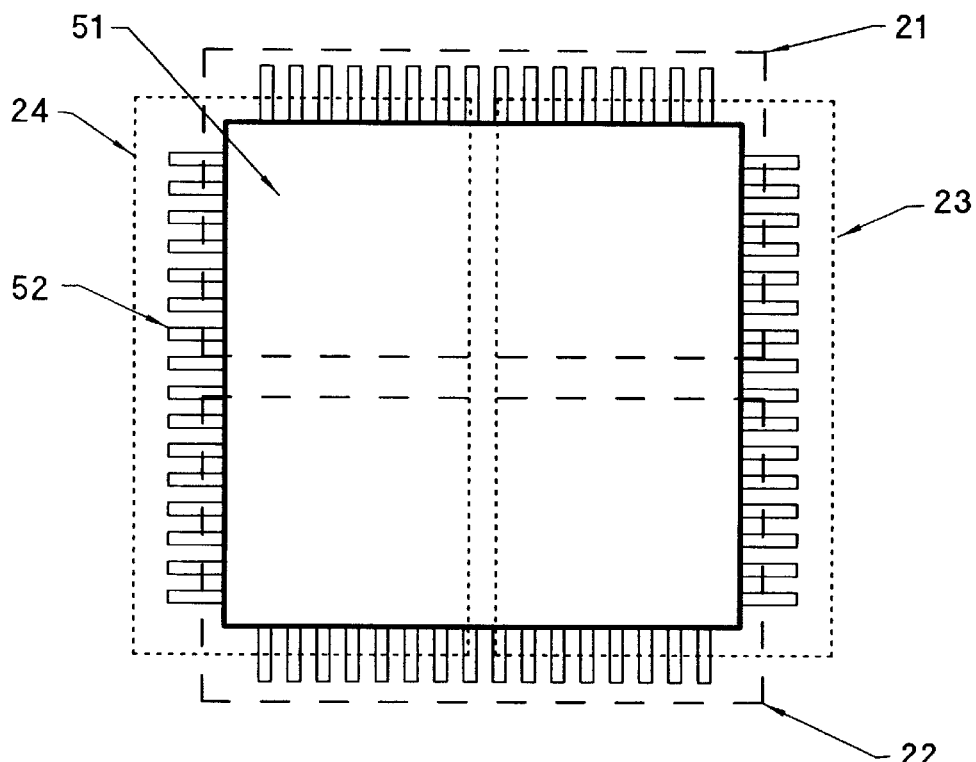
FIG. 7 illustrates a plan view of a quad flat pack IC with superimposed field of view of the four oblique monochrome cameras.

The four obliquely mounted monochrome cameras 3,4, 5 and 6 are responsible for the acquisition of images containing IC leads. For example, the leads 52 (see FIG. 7) on the four sides of a quad flat pack IC 51 can be seen by the four monochrome cameras 3,4, 5 and 6. The leads 52 on each side of the IC 51 is viewed by one of the four oblique monochrome cameras 3, 4, 5 and 6. In the case where an IC is larger than the fields of view of the oblique monochrome cameras, then several acquisition steps must be carried out to cover the leads 52 completely. The move and acquire action is accomplished by the X-Y table which will be described in further detail.

Figure 8:
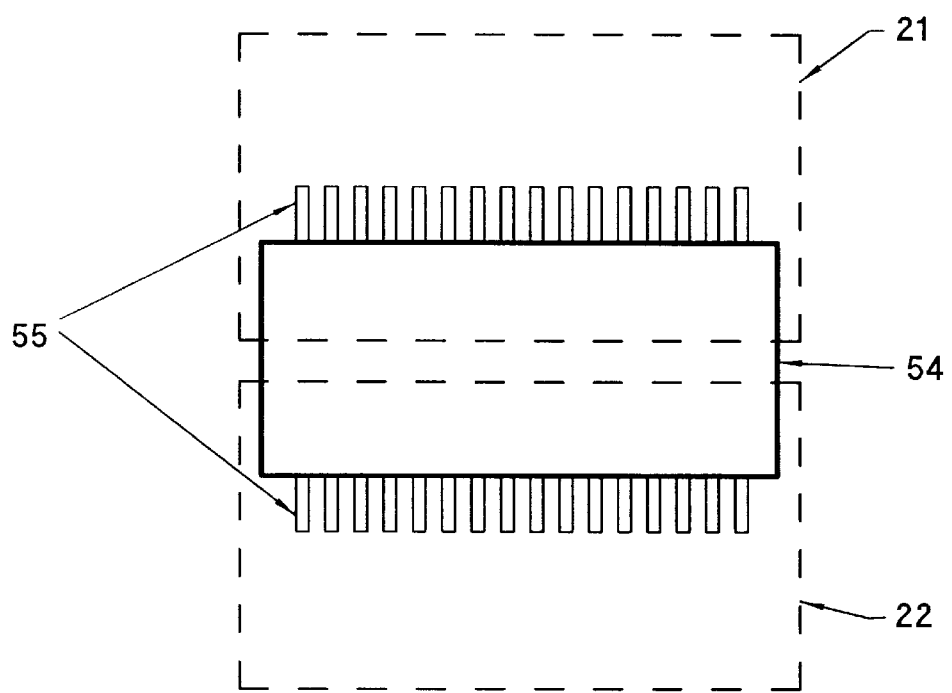
FIG. 8 illustrates a plan view of a small outline IC (SOIC) with a superimposed field of view from two opposite facing oblique monochrome cameras.

For the case of dual-sided IC's, such as the SOIC 54 (see FIG. 8), then only one pair of oblique monochrome cameras need to be used to view the leads 55. For example, if the SOIC 54 is mounted with its long side aligned in the East–West direction, then only the North 5 and the South 6 cameras are required to view the leads 55. As each of the four oblique monochrome cameras 3, 4, 5 and 6 are tilted with respect to the PCB assembly 1, height related information can be obtained. The variation in height of a component is translated as a shift in the position of the components. Lifted lead defect involves a change in the height of the lead and hence can be detected as a change in its position in the image captured by the oblique viewing cameras.

The ring-shaped, white light source 7 is used in the present embodiment. The ring-shaped, white light source 7 is mounted around the center color camera 2 and illuminates the PCB assembly 1 from the top with uniform distribution of light. The ring-shaped, white light source 7 has the opening 10 in its center. The clear opening 10 enables the center color camera 2 to view the PCB assembly 1 without obstruction. The ring-shaped, white light source 7 enables different color spectrum to be equally illuminated and hence facilitates color image processing and analysis. The use of a ring-shaped, white light source 7 with associated color image processing is especially useful to detect colored components, such as surface mounted resistors and capacitors. Some of these components may be brown, yellow, blue or orange in color. If only monochrome images are used, then it will not be possible to distinguish the colored components from the background. In monochrome images, the color of the PCB and the colored components may appear to have almost the same shade of grey, hence projecting no contrast to facilitate detection.

The ring-shaped, white light source 7 has a strong intensity output such that the ambient lighting condition will not affect the actual inspection condition. Quantitatively, intensity of the ring-shaped, white light source 7 is more than ten times stronger than the ambient lighting level. Strong lighting intensity also allows the aperture, also known as an iris, of the camera lens to be adjusted small, hence increasing the depth of field of the cameras. This is especially important for the four oblique monochrome cameras 3, 4, 5 and 6. The size of the aperture is inversely related to the depth of field of an imaging system. A large depth of field renders the imaging systems less susceptible to the change in the height or depth of the object under inspection. The change in depth and height of the PCB assembly 1 may arise from the change in components' dimensions, the thickness 17 of the PCB and/or the warpage 16 of the PCB. These are undesirable changes and will affect the clarity of the images acquired by the cameras 2, 3, 4, 5 and 6. Having a large depth of field enables well-focused images to be captured regardless of these variations. Furthermore, each of the monochrome cameras 3, 4, 5 and 6 mounted at an oblique angle 11 to the PCB assembly 1 needs a large depth of field to view the entire field of view clearly. The near field and far field of an oblique viewing camera will have different depths as denoted by 15.

The size of the PCB assembly 1 is usually much larger than the fields of view of the cameras. Hence, the PCB assembly 1 is divided into many different segments, one of which is inspected at a time. An X-Y table 62 is required to move each of the segments of the PCB assembly 1 to the camera and lighting assembly 12 for inspection. Each segment may consist of different components or IC's. The practical size of the field of view 20 of the center color camera 2 is determined by the smallest component size that can be found on the PCB assembly 1. A surface mount component as small as 1.0 mm by 0.5 mm can be found. Hence, the pixel resolution of 30–50 microns ($10^{-6}$ m) is required for the center color camera 2. The field of view is measured by the horizontal width (H) and vertical width (V). The horizontal factor of the field of view 20 is equal to the total number of pixels in the horizontal direction multiplied by the pixel resolution.

Figure 3:
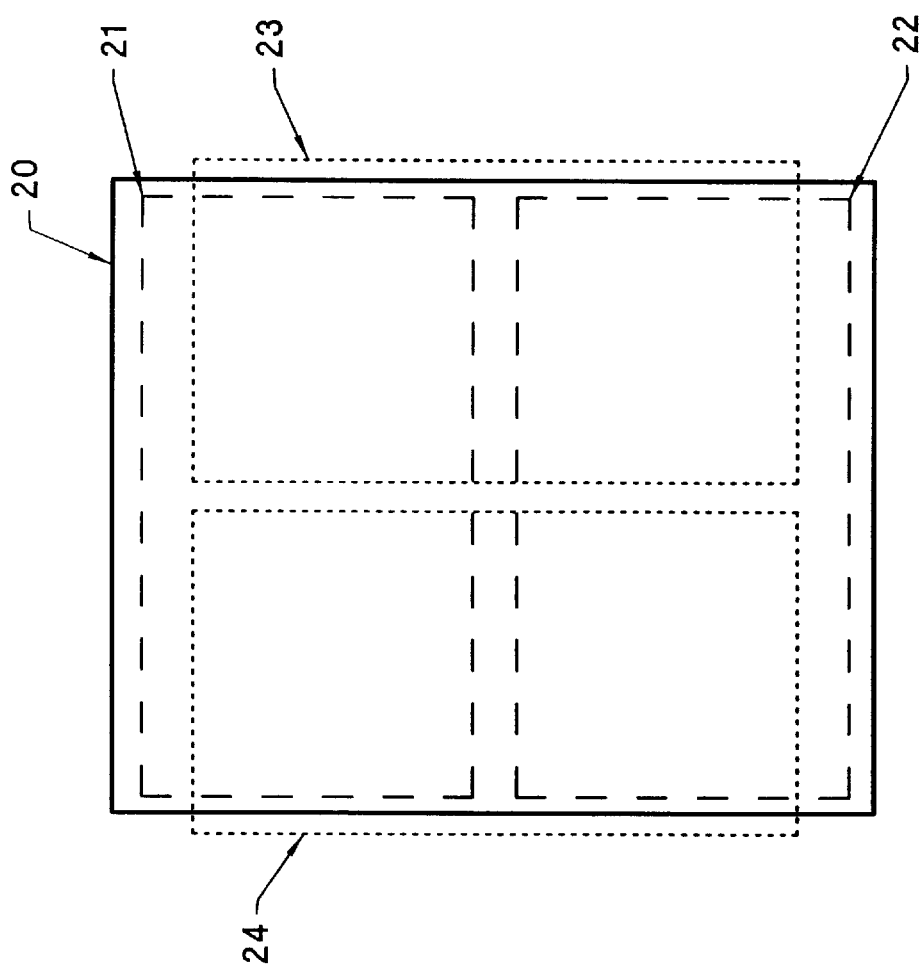
FIG. 3 illustrates a field of view arrangement.
Figure 4:
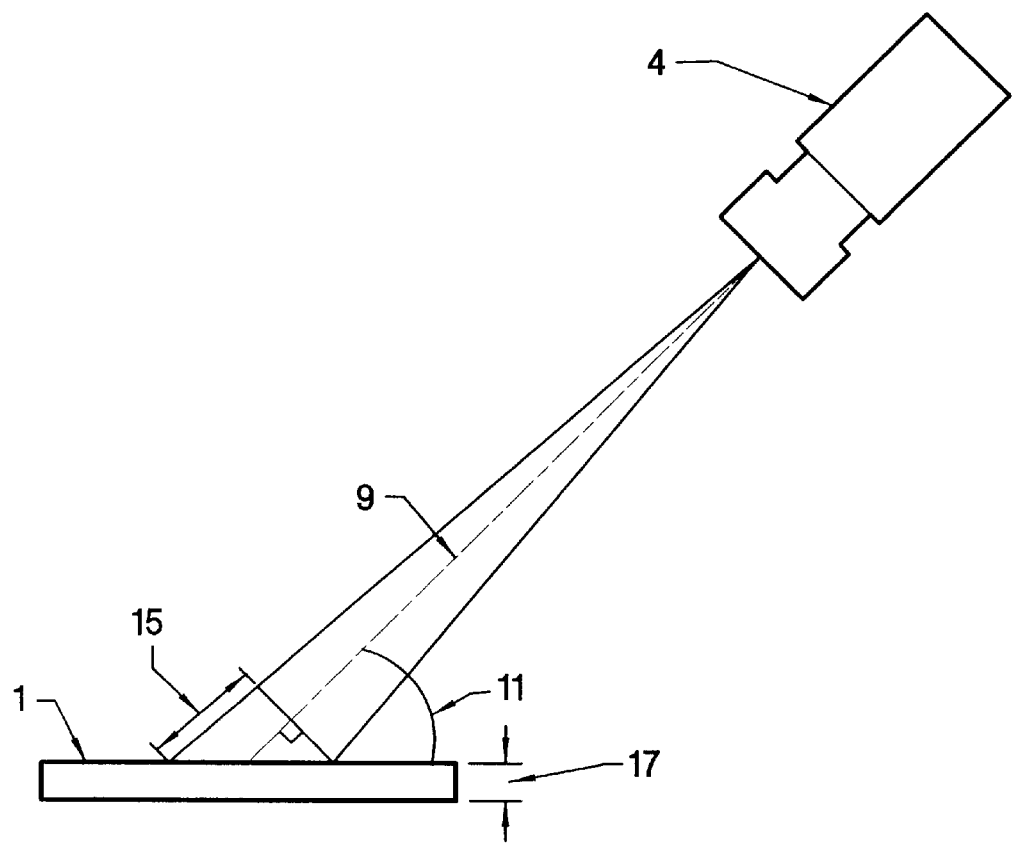
FIG. 4 illustrates the depth of field for oblique view compensation.
Figure 5:
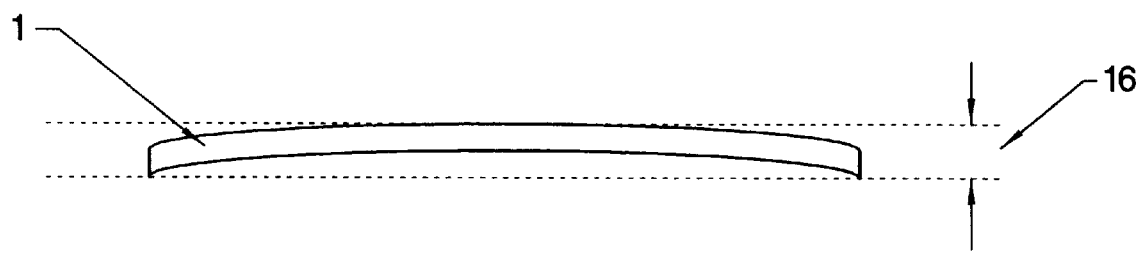
FIG. 5 illustrates the depth of field for warpage compensation.
Figure 6:
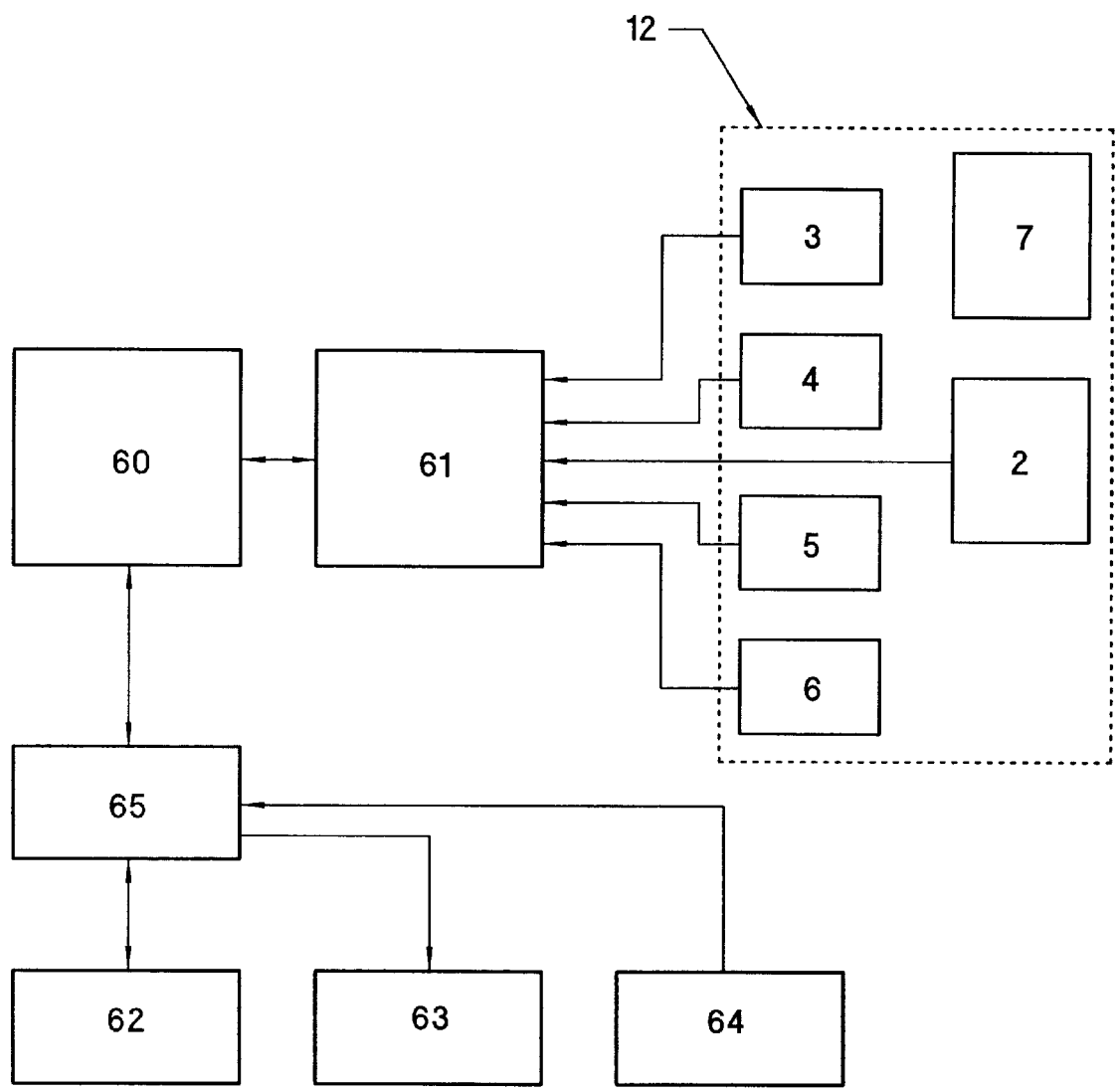
FIG. 6 illustrates a block diagram of the overall system setup.

Similarly, the vertical factor of the field of view is equal to the total number of pixels in the vertical direction multiplied by the pixel resolution. A pixel resolution of 20–30 microns is required for each of the oblique monochrome cameras 3, 4, 5 and 6. The effective fields of view 21, 22, 23 and 24 of the oblique monochrome cameras 3, 4, 5 and 6 are smaller than that of the center color camera 20. Hence, a large overlap exists between the fields of view of the center color camera 2 and the four oblique monochrome cameras 3, 4, 5 and 6 as illustrated in FIG. 3. The pixel resolution is a trade-off between the speed of inspection and the accuracy of inspection. For example, if the pixel resolution is smaller than 20 microns, it will enable defects, such as a lifted lead, to be detected with ease. However, if the field of view coverage is small and more X-Y stepping has to be carried out, an increase in the overall inspection time results.

In the present embodiment, a rule-based approach for detecting defects on the PCB assembly 1 is used. Signatures are extracted from the plurality of images acquired by the color and monochrome cameras 2, 3, 4, 5 and 6. The signatures are verified with a set of rules for determining the condition of the PCB assembly 1. The rule-based approach means that there is no need to memorize the images of a known good PCB assembly 1. Hence, memory requirements are reduced in the image processing system as well as the computational speed.

The signatures that can be extracted include the X and Y projections of the leads and body of the components and IC.

Using the X and Y projections, several other parameters can be further extracted such as the number of transitions, the distance between transitions, and the pitch between the transitions. These signatures are normalized so that they are less susceptible to changes in illumination conditions.

The overall system setup includes a personal computer (PC) which is used as the host 60. The PC host 60 is connected to frame grabbers 61 and a programmable logic controller (PLC) 65. The PC host 60 coordinates the entire inspection activities. The frame grabbers 61 are further connected to the five cameras 2, 3, 4, 5 and 6. The frame grabbers 61 receive the video sources from the five cameras 2, 3, 4, 5 and 6 and digitize them in a form suitable for digital image processing. The frame grabbers 61 are equipped with image processors for digital image processing purposes. The PLC 65 receives inputs from a set of sensors 64. These sensors 64 are used to sense the presence of a PCB assembly on the conveyor 63, home position and/or other safety features. The PLC 65 controls the X-Y table 62 which is responsible for moving the PCB assembly 1 segment-by-segment to the camera and lighting assembly 12 for inspection purposes.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. An apparatus for inspecting an IC on a printed circuit board assembly, the IC having leads extending from four sides, the apparatus comprising:
    a lighting assembly for illuminating the printed circuit board assembly, and
    a plurality of cameras for viewing the printed circuit board assembly, the plurality of cameras including:
        a center camera having an optical axis arranged substantially perpendicularly to the printed circuit board assembly; and
        two opposing pairs of surround cameras arranged such that their respective optical axes are positioned symmetrically about the optical axis of the center camera and the axes are arranged obliquely with respect to the printed circuit board assembly such that each opposing pair of surround cameras has two associated fields of view on the printed circuit board assembly,
        wherein the two fields of view of each opposing pair of surround cameras do not overlap and the two fields of view are separated to enable the leads on two opposite sides of the IC to be separately viewed by the opposing pair of surround cameras.

2. The apparatus as in claim 1, wherein the two opposing pairs of cameras have substantially similar magnification factors.

3. The apparatus as in claim 1, further comprising video signals representative of the images acquired by the two pairs of cameras, wherein the video signals associated with the two pairs of cameras are subsequently processed using substantially similar image processing algorithms.

4. The apparatus as in claim 1, wherein the lighting assembly further comprises a white light source for providing uniformly distributed white light, the intensity of which is at least ten times stronger than ambient light.

5. The apparatus as in claim 4, wherein the white light source is ring-shaped and it is disposed so that the optical axis of the center camera extends through the opening defined by its ring-shaped structure.

6. The apparatus as in claim 1, further comprising an X-Y table for supporting the printed circuit board assembly and moving it in the X-Y plane.

7. A method for inspecting an IC on a printed circuit board assembly, the IC having four sides with leads extending from each side, the method comprising:
    illuminating the printed circuit board assembly,
    viewing the printed circuit board assembly using a plurality of cameras, the plurality of cameras including:
        a center camera having an optical axis arranged substantially perpendicularly to the printed circuit board assembly; and
        two opposing pairs of surround cameras arranged such that their respective optical axes are positioned symmetrically about the optical axis of the center camera and the axes are arranged obliquely with respect to the printed circuit board assembly such that each opposing pair of surround cameras has two associated fields of view on the printed circuit board assembly,
        wherein the two fields of view of each opposing pair of surround cameras do not overlap and the two fields of view are separated to enable the leads on two opposite sides of the IC to be separately viewed by the opposing pair of surround cameras,
    forwarding video signals from the plurality of cameras to at least one frame grabber; and
    processing the video signals to detect defects in the leads of the IC.

8. The method as in claim 7, wherein the step of viewing the printed circuit board assembly using a plurality of cameras comprises the step of using the two pairs of cameras having substantially similar magnification factors.

9. The method as in claim 7, further comprising the steps of: representing the images acquired by the plurality of cameras with video signals; and processing the video signals associated with the two pairs of cameras using substantially similar image processing algorithms.

* * * * *